United States Patent [19]

Lentz

[11] Patent Number: 4,708,713
[45] Date of Patent: Nov. 24, 1987

[54] METHOD AND SYSTEM FOR REMOVING IMMUNOSUPPRESSIVE COMPONENTS FROM THE BLOOD OF MAMMALS

[75] Inventor: M. Rigdon Lentz, Irvine, Calif.
[73] Assignee: Anisa Medical, Inc., San Diego, Calif.
[21] Appl. No.: 671,990
[22] Filed: Nov. 16, 1984
[51] Int. Cl.$^4$ ............................................. A61M 37/00
[52] U.S. Cl. ......................................................... 604/5
[58] Field of Search ........................................ 604/4–6; 128/1 R

[56] References Cited

U.S. PATENT DOCUMENTS

| Re. 31,688 | 9/1984 | Popovich et al. | 604/6 |
| 4,116,589 | 9/1978 | Rishton | 604/4 |
| 4,191,182 | 3/1980 | Popovich et al. | 604/6 |
| 4,350,156 | 9/1982 | Malchesky et al. | 604/6 |

FOREIGN PATENT DOCUMENTS

| 0076665 | 4/1983 | European Pat. Off. | 128/1 R |
| 3302384 | 7/1984 | Fed. Rep. of Germany | 604/4 |
| WO79/01121 | 12/1979 | PCT Int'l Appl. | 210/90 |
| 2136314 | 9/1984 | United Kingdom | 604/4 |

OTHER PUBLICATIONS

*IBM Technical Disclosure Bulletin*, vol. 19, No. 3, Aug. 1976, pp. 765–768.

Primary Examiner—C. Fred Rosenbaum
Assistant Examiner—Jerome R. Smith, Jr.
Attorney, Agent, or Firm—Fulwider, Patton, Rieber, Lee & Utecht

[57] ABSTRACT

The invention relates to a method and system for extracorporeally treating the blood of a patient having diseased tissue or a condition, such as cancer, which results from or depends upon a dysfunction of the patient's immune system. In accordance with the invention, blood is withdrawn from the pateint, a low molecular weight fraction of the blood containing immunosuppressive components which retard or prevent immune system responses is selectively separated from the withdrawn blood, preferably by means of an ultrafilter, and treated blood is returned to the patient to initiate an immune response.

13 Claims, 3 Drawing Figures

METHOD AND SYSTEM FOR REMOVING IMMUNOSUPPRESSIVE COMPONENTS FROM THE BLOOD OF MAMMALS

BACKGROUND OF THE INVENTION

This invention generally relates to an improved extracorporeal method and system for treating diseases and conditions resulting from or dependent upon deficiencies in the immune response system, and particularly for treating cancer and other neoplastic tissue in mammals by reducing the levels of immunosuppressive components in the blood.

It is widely recognized that the cell mediated immune system will, under normal circumstances, attack and destroy cancer cells and other neoplastic tissue. However, the cell mediated immune response is sometimes suppressed or blocked by one or more factors and when this dysfunction or dysregulation occurs the disease or condition (e.g., pregnancy) can develop and progress relatively unimpeded.

The nature and operational characteristics of the factor or factors which block or suppress the cell mediated immune system are for the most part unknown. Research has shown that these modulating factors exist in serum and that by removing these factors the serum will again allow a normal immune response.

Much of the work to date relating to the immunosuppressive activities of the blocking factors has been in vitro testing of cancer cell interactions with autologous lymphocytes. While the cytotoxic effects on cancer cells which have been incubated in serum treated in various ways to reduce the effects of the blocking agents has shown that cancer patients do have a lymphocyte population that can recognize and destroy cancer cells, there has been little or no progress in the development of treatment procedures for patients with immune deficiency diseases by any of the treatments used in such research.

One attempt to extracorporeally treat a patient's blood to mitigate the effects of an immune deficiency is found in European Patent Application No. 79,2211. In the process described in this patent application, blood is removed from a cancer patient and subjected to plasmaphoresis to separate plasma from the blood cells and then the plasma is perfused over a charcoal bed which has been coated with immobilized protein A. The plasma so treated is then remixed with the blood cells and returned to the patient. Significant immune response was noted against cancer tissue in these patients. Because the plasmaphoresis process used to separate the blood cells from the plasma has a serious impact on the platelet level in the blood, this process could not be considered for widespread use in a variety of patients, particularly those in the serious conditions of advanced cancers and in autoimmune diseases. Furthermore, the processing steps of first separating the blood into a fraction of packed cells, a bulky coat layer and a fraction of plasma by plasmaphoresis and then treating the plasma in the manner described are not very attractive for clinical use.

Thus, notwithstanding all the outstanding work which has been done on immunosuppressive effects of blocking factors, particularly the work in the last 15 to 20 years, there still remains the obvious and widespread need of a safe, simple and inexpensive method and system which can treat or control diseases or conditions resulting from immune system disregulation in a clinical setting.

The present invention was developed in response to these well known and widespread needs and satisfies the many requirements thereof.

BRIEF DESCRIPTION OF THE INVENTION

This invention generally relates to a method and system for treating immune deficiency diseases and conditions in mammals wherein the immune response of such mammals is improved by removing immunosuppressive components from the blood thereof. This method and system is particularly suitable for treating human patients with cancer or other neoplastic tissue. The process has essentially no side effects and the risks involved are no greater than with dialysis. Moreover, patients can be readily treated on an outpatient basis.

In accordance with the invention, blood is withdrawn from a mammal (hereinafter "patient") having an immune response dysfunction, the blood is treated to selectively separate therefrom a low molecular weight blood fraction which contains the immunosuppressive components thereof and then the treated blood is returned to the patient to initiate an acute immune response in order to control or cure the immune deficiency disease or condition. In a preferred embodiment of the invention, the blood of the patient is passed through an ultrafilter to remove therefrom immunosuppressive components having molecular weights of less than about 1,000,000 Daltons, and particularly those having molecular weights less than about 200,000 Daltons which are believed to be primarily responsible for blocking the cell mediated immune response.

When significant quantities of a patient's blood are to be treated, e.g., more than about 15% of the total blood volume, care must be exercised to return to the patient nutrients, vitamins, salts and other necessary blood components which are removed from the blood by the ultrafiltration or other separation process. Preferably these necessary blood components are returned to the patient in a volume of liquid which is at least equivalent to the volume of liquid which is separated from the blood with the low molecular weight fraction containing the immunosuppressive components.

Although the present method and system are described herein as being primarily concerned with the treatment of cancer, the method and system is fully applicable to immune dysfunction diseases such as multiple sclerosis, acquired immune deficiency syndrome (AIDS), lupus erythematosus, rheumatoid arthritis and other autoimmune diseases. In addition, the process may be used to initiate labor in pregnant mammals. While at first glance, pregnancy does not appear to be an immune deficiency disease or condition, it is believed that the blocking factors which prevent the normal immune mechanism from rejecting the fetus in pregnant mammals operate in essentially the same manner as in immune deficiency diseases. Once the immunosuppressive factors are reduced to a sufficiently low level in the blood of a pregnant mammal, the body starts to reject the fetal tissue in a series of cellular events that are essentially the same rejection found in organ transplants.

The response of a cancerous tumor to the treatment in accordance with the present invention is most dramatic. Within a few hours following treatment the tumor becomes erythemic and, if near the skin, warm to the touch indicating early inflammation of the tumor.

Within 24 hours of treatment, the tumor becomes edematous or swollen, softer and remains inflamed and warm. Biopsy of the tumor at this time reveals perivascular cuffing, edema and vascular engorgement and at 48 hours indicates hemorrhaging of the tumor and lymphocytic infiltration. After 72 hours the tumor becomes soft and detached from underlying tissue. A biopsy from about 72 hours up to 2 weeks after treatment shows acute and chronic lymphocytic infiltration into the tumor which is attended by massive tumor cell necrosis or death with complete sparing of the adjacent normal tissue. The process is believed to be a immunological attack specific to the cancer and is for the most part identical to the acute rejection found in organ transplantation. There is no evidence of any damage to adjacent noncancerous tissue from the process.

The above features and advantages will become more apparent from the following detailed description of a preferred embodiment when taken in conjunction with the attached drawings.

DETAILED DESCRIPTION OF THE INVENTION

In accordance with the present invention, blood is preferably removed from the patient through a venous catheter which has been inserted through a suitable vein such as the jugular or the cephalic vein into the superior vena cava for small animals such as dogs and the brachiocephalic and subclavian veins for human treatment. Blood is withdrawn from the catheter and directed by a suitable pump and tubing to a separation-means such as an ultrafilter wherein a low molecular weight blood fraction containing immunosuppressive components in the blood is selectively separated therefrom. After the blood is treated it is returned to the patient through a suitable venous catheter to thereby initiate an acute immune response. Nutrients, salts, vitamins and other necessary blood components, which are removed from the blood by the separation process are preferably returned to the patient in a volume equivalent to the volume of permeate separated from the blood. The treatment process continues until the immunosuppressive components in the body are reduced to a level which allows an acute immune response or until the effects of removing the blocking agents become evident in the patient, e.g., the pregnant mammal goes into labor.

Figure 1:
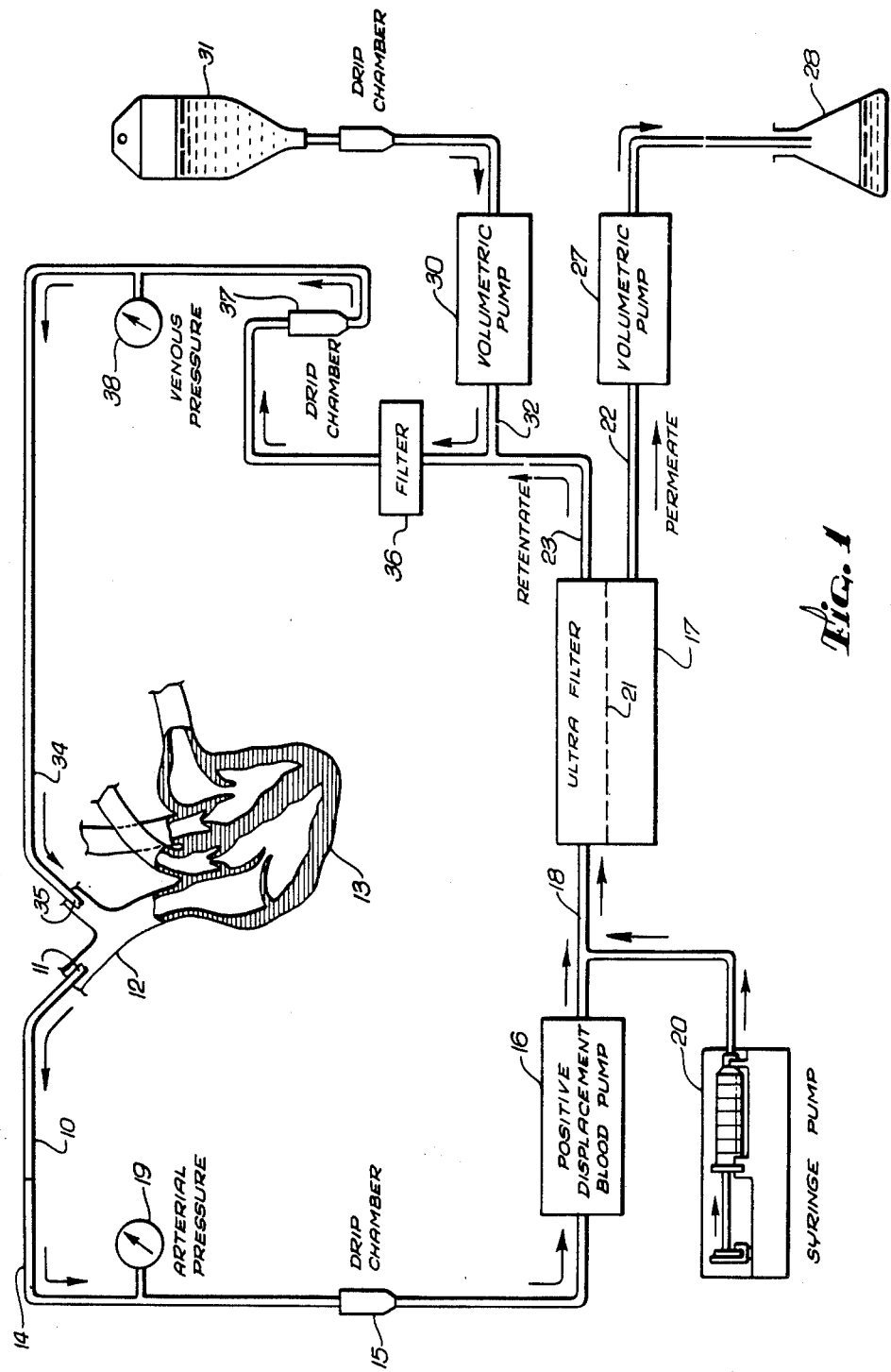
FIG. 1 schematically illustrates a system for locating blood which embodies the present invention.

With particular reference to FIG. 1 which illustrates a preferred embodiment, blood is removed from a patient by means of a venous catheter 10 with the distal end 11 thereof disposed in the superior vena cava 12 leading to the patient's heart 13.

The blood passes through conduit 14 to a drip chamber 15 and then onto pump 16 which controls the pressure of the blood to the separation unit 17 preferably an ultrafilter as shown, through conduit 18. A pressure gauge 19 is provided on conduit 14 to continually monitor arterial pressure. A syringe pump 20 feeds an anticlotting drug such as sodium heparin to conduit 18 to prevent the clotting of blood in the ultrafilter 17. In the ultrafilter 17 the blood stream passes over the ultrafilter medium or membrane 21 under pressure. The blood fraction having low molecular weight components, e.g. those having molecular weight less than about 1,000,000 Daltons, preferably less than about 200,000 Daltons, passes through the membrane 21 and is discharged as permeate through conduit 22. The retentate or treated blood containing the high molecular weight components, which include whole blood cells and platelets, is discharged into conduit 23 which ultimately leads back to the patient. Volumetric pump 27 passes a controlled amount of permeate to a graduated erlenmeyer flask 28 for containment and for measuring. Volumetric pump 30 which is preferably the same type and capacity as pump 27, pumps nutrients, salts, vitamins and other necessary blood components from a bottle 31 containing same to conduit 32 which directs the fluid to conduit 23 where it mixes with the retentate or treated blood. The treated blood and other components are returned to the patient through venous catheter 34, the distal or discharge end of which is disposed in the brachiocephalic vein. The volumetric pumps 27 and 30 are preferably set either to pump the same total amount of fluid or to pump at the same rate, so that the same volume of fluid which is removed from the patient's blood stream as permeate is returned with the necessary salts, nutrients, vitamins, etc. The blood stream in conduit 23 is passed through filter 36 to remove clots or other debris from the blood stream. A drip chamber 37 ensures that no significant quantities of air enter the patient's blood stream. A pressure gauge 38 is provided to continually monitor venous blood pressure.

Figure 2:
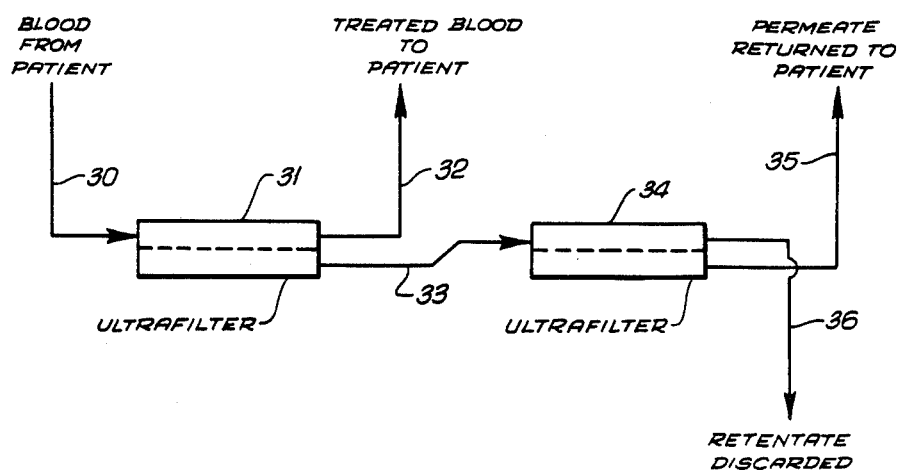
FIG. 2 illustrates a preferred ultrafiltration system.

FIG. 2 illustrates another embodiment wherein blood removed from a patient is first passed through conduit 30 to a first ultrafilter 31 to selectively separate a blood fraction with components having molecular weights less than about 1,000,000 Daltons. The retentate from this ultrafiltration which contains the high molecular weight components is returned through conduit 32 to the patient. The permeate from the first ultrafilter 30 is passed through conduit 33 to a second ultrafilter 34 where a blood fraction having a molecular weight below 30,000 is removed from the permeate stream from the first ultrafilter 30. The permeate from the second ultrafilter 34, which contains the very low molecular weight components such as salts, nutrients and the like, may be returned to the patient through conduit 38. The retentate from the second ultrafilter which contains blocking factors, IgG immunoglobulins and other components is discharged through conduit 36 and 13.

It should be noted that the process of the invention can also be used to remove IgG immunoglobulins which are useful in the treatment of arthritis or other diseases.

The ultrafilter medium or membrane should have an effective pore size less than about 15 microns in diameter in order to selectively separate the desired low molecular weight components from the blood. A filter media having an effective pore size of about 0.07 to about 0.1 microns will separate components with molecular weights less than about 1,000,000 Daltons, whereas filter media having an effective pore size of about 0.03–0.07 microns will separate components with molecular weights less than about 200,000 Daltons. A membrane with an effective pore size less than about 0.03 micron is needed to separate blood components with molecular weights less than about 30,000 Daltons.

A preferred membrane is one in which the pores are made by electron beams directed perpendicularly to the surface because in this manner the size and density of the pores can be accurately controlled. The pores are essentially circular in cross section so the effective pore size is the actual pore size. The effective pore size of ultrafiltered media having pores with non-circular cross sections shall be the diameter of a circular pore which will pass molecules or other components of an equivalent size to the molecules or other components which pass through the filter medium in question.

The filter membrane should be less than about 25 microns, preferably less than about 10 microns thick. Suitable materials for the ultrafilter membrane include sheets of polytetrafluorethylene (Teflon R) and polycarbonate resins. The permeable membrane should not cause blood clotting or otherwise react with the blood.

Blood should be pumped through the ultrafilter unit at sufficient pressure to cause the blood components having the immunosuppressive effects to pass through the filter but at a velocity which will not excessively shear or otherwise damage the blood cells passing over the membrane. Generally it has been found that the ratio of the area of the membrane to the amount of blood treated per hour should be within about 0.1 to 2 $Cm^2/mL$. Differential pressure across the membrane should range from about 2 to 20 mM Hg.

Figure 3:
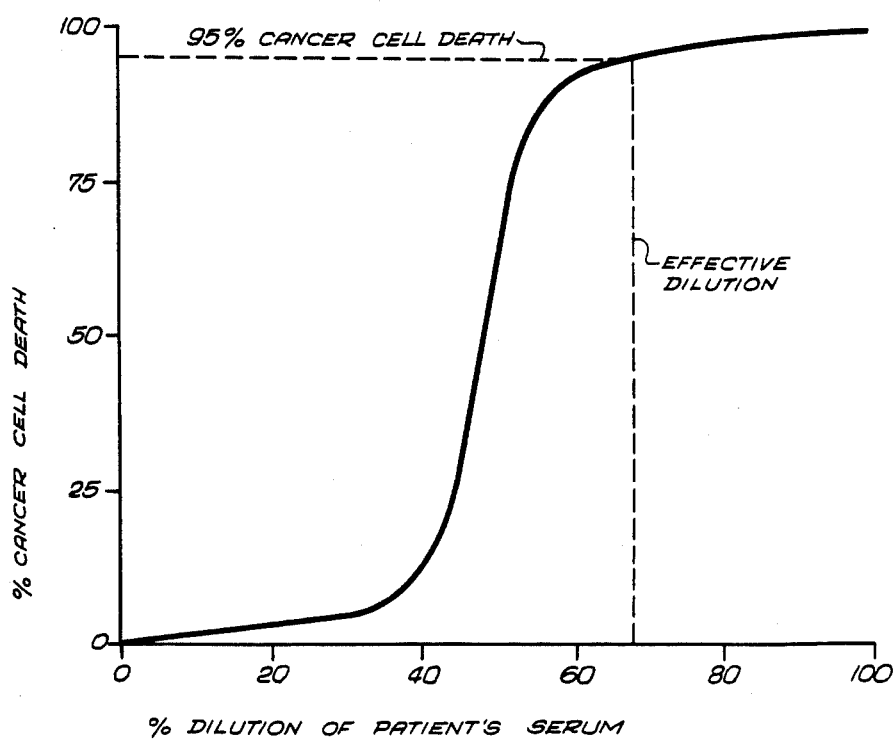
FIG. 3 is a graph generally illustrating the relationship of the percent of cancer cell death to the dilution of cancer patient's serum with a serum free of blocking factors.

In the treatment of patients with cancer, it is important to determine the minimum amount of the blood fraction containing the immunosuppressive components which must be removed to effectively initiate an accute immune response. For this determination, a biopsy of the tissue in question is taken and the biopsy specimen is incubated with a solution of radioactive chromium, i.e. $^{(51)}Cr$, or iridium for about 1 to 2 hours during which time the radioactive material diffuses into the biopsied tissue cells. Following the incubation period, the radioactive tag solution is drained away from the cells and the cells washed copiously with tissue culture media to remove essentially all traces of the radioactive tag from the surface of the cells. Specimens of the cancerous tissue are mixed in vitro with serum from the patient which has been diluted to various concentrations with a serum free of the blocking agent such as normal human serum or fetal calf's serum. Dilution of 0% and 100% serum were used to obtain the end points. The patient's T-lymphocytes were obtained from a sample of the patient's blood and were washed free of the patient's serum. T lymphocytes were then added to the tumor cells-serum mixtures at a ratio of about 10 lymphocytes to each cancer cell and then incubated. During incubation the T-lymphocytes attack and destroy the cancer cells and in the process the cancer cells release radioactive material into the surrounding solution or medium. After 24 or 36 hours the remaining T-lymphocytes and cancer cells are filtered from the culture media and the media is placed in a gamma counter to determine the amount of the radioactive tag therein. The incubating well containing the 0% dilution is taken as essentially no cancer cell death and 100% dilution as 100% cancer cell death with the other dilutions falling therebetween. Generally, it is believed that the dilution which will provide an excellent cancer cell death in vivo is one that will provide at least a 95% in vitro cancer cell death in the above test. FIG. 3 illustrates the general relationship of cell death to serum dilution. As cancer growth progresses, the curve will shift toward higher dilutions indicating more extensive treatments are necessary. On the other hand, as pregnancy progresses, the curve will shift to lower dilutions, indicating less extensive treatments to bring on labor.

The immunosuppressive or blocking factors are contained in essentially all extracellular fluids within the body, but only the blood is really suitable and readily available for treatment. Therefore, the dilution of the fraction of the blood containing these blocking factors needed for an acute cell mediated immune response is calculated on the amount of extra cellular fluids in the body of the patient. For humans the amount of extracellular fluids is usually estimated to be about 20% of the patient's less body mass. Thus, if the radioactive chromium test indicates that a dilution of 50% is required for an effective immunological response and if the patient lean body mass was, for example, 150 pounds, then the amount of the whole blood which must be treated by ultrafiltration is as follows:

$$150 \text{ lbs.} \times 0.20 \times 0.50 = 15 \text{ lbs.}$$

Thus in the above example, 15 pounds of the patient's blood would have to be passed through the ultrafiltration unit.

In the treatment of cancer and other similar immune deficiency diseases, multiple treatments of the blood are usually necessary to effectively cure the cancer or other disease or at least reduce the tumor to a size and/or condition where it can be removed by surgery or treated by other techniques. In pregnancy, the patient is usually treated until the effects of removing or reducing the immunosuppressive factors become evident in the patient, i.e., labor begins.

While the aforesaid description of the invention has been primarily directed to removing the immune blocking factors in the blood fraction having molecular weights less than 200,000, there appears to be two separate immunosuppressive or blocking fractions in the blood and other extracellular fluids in the body. One fraction, as previously described, has a molecular weight of less than about 200,000 and appears to be primarily responsible for blocking the cell mediated immune response. It is believed to be an IgG type immunoglobulin molecule. The other fraction has a molecular weight between about 200,000 and 1,000,000 and is believed to be an immune complex.

At the start of the procedure for treating blood in the aforesaid system, the entire system should be first flushed with a compatible plasma and then treated with an anticoagulant or anticlotting agent, such as sodium heparin, to be sure that there are no locations within the system where blood clotting can occur. Moreover, small amounts of anticoagulants should be continually introduced into the blood stream directed to the ultrafilter to ensure that no clotting occurs during the filtration process. All of the surfaces of the system which come in contact with the blood and fluids which are infused into the patient must be sterilized prior to commencing treatment.

The following examples are provided to further illustrate a preferred embodiment of the invention.

EXAMPLE 1

A ten year old female cocker spaniel, having a malignant breast tumor identified as carcinoma was treated in accordance with the invention to remove the immunosuppressive factors from the dog's blood so that the dog's cell mediated immune system could properly function and thereby control the growth of this tumor. The dog's tumor was firm, about 5 cm in lateral dimension, about 4 cm in its cephalocaudel dimension and about 2.5 cm in depth, and was well attached to the underlying deep musculature. For the treatment, two small venous catheters were inserted into the right jugular vein of the dog so that the distal end of one of the catheters was placed in the right brachiocephalic vein and the distal end of the other was approximately 4 cm away from the first and positioned in the superior vena cava. Approximately 75 cc's per minute of blood was withdrawn from the dog through the catheter positioned in the superior vena cava and pumped to an ultrafilter which had a permeable membrane with 50 square centimeters of effective surface area and with an average pore size of about 0.05 microns in diameter. The permeate pump was adjusted to withdraw 2 cc's per minute of permeate from the ultrafilter, and a second pump withdrew plasma from a source bottle and pumped the plasma into the discharge conduit of the ultrafilter at the same rate as the permeate was withdrawn from the ultrafilter. The plasma included sodium, potassium, vitamins and other necessary nutrients. The ultrafiltration of the patient's blood was continued for about one hour until 125 cc's of permeate had been removed from the ultrafilter. Within 3½ hours after the treatment the tumor area was found to be inflamed and warm to the touch indicating significant immunological activity. No clinical side effects were noted from the procedure. Within 24 to 48 hours of the treatment, the size of the dog's tumor had increased by almost 25% and was softer than prior to the treatment and clearly edematous. A second equivalent treatment was given to the patient 2 days after the first and similar results were obtained. The tumor had softened considerably and had started to become disengaged from the underlying musculature system. After a third equivalent treatment, the tumor size had been reduced and the tumor had begun to liquify. A biopsy, performed two days after the third treatment, indicated that the muscle tissue underlying the tumor had no traces of cancer cells and massive tumor cell necrosis was observed with the complete sparing of the surrounding normal tissue. Also evident was prominent perivascular cuffing of lymphocytes in a classical fashion characteristic of acute tissue rejection.

EXAMPLE 2

A four year old Golden Labrador Retriever having a poorly differentiated osteogenic sarcoma with a very high mitotoxic index in the distal end of the left humerus and the proximal end of the radius and ulna was treated in accordance with the invention. The tumor was rock hard and the joint measured 11½ inches in comparison with 8½ inches for the right elbow joint. The dog was subjected to eight treatments over a ten day period essentially equivalent to that described in Example 1. The amount of ultrafiltrate removed during each treatment was as follows:

| Treatment No. | Permeate, cc |
| --- | --- |
| 1 | 318 |
| 2 | 716 |
| 3 | 360 |
| 4 | 500 |
| 5 | 300 |
| 6 | 300 |
| 7 | 300 |

-continued

| Treatment No. | Permeate, cc |
| --- | --- |
| 8 | 300 |

A biopsy of the tumor after three treatments revealed intense perivascular cuffing of blood vessels feeding the tumor, necrosis of osteogenic sarcoma cells and extensive inflammatory infiltration into the tumor of polymorphonuclear leucocytes, activated lymphocytes, plasma cells and monocytes all of which indicate acute cell mediated attack on the tumor. Surgical debridement three weeks after the last treatment found massive tumor necrosis.

EXAMPLE 3

Four pregnant goats were treated in accordance with the invention to determine the effects of such treatment on the pregnancy of these animals. One of the goats was at 35 days of gestation, two of them were at 2½ months of gestation and one at 4½ months gestation. The system was essentially the same as that used in Example 1. The blood flow rate from the goats to the ultrafilter ranged from about 100 to 600 cc per minute. The area of the permeable filter media was about 144 cm and the average pore diameter in the membrane was about 0.05 microns. The differential pressure across the membrane ranged from about 40 to 80 mm Hg and permeate withdrawal rate range from about 6 to 11 cc per minute. Treatment times varied from about 2 to 5 hours. In each case labor began shortly after the treatment began and all of the goats aborted within 48 hours with no apparent clinical side affects.

EXAMPLE 4

A female human patient having malignant growths in both lungs, a tumor in the left shoulder area identified as adenocarcinoma and tumor sites in the cervical spinal area was treated in accordance with the invention. Blood was withdrawn from the patient through a Quinton DD dialysis catheter which had been inserted through the patient's right subclavian vein. The distal end of the dual catheter was placed in the superior vena cava. During the treatments, the filtered blood returned to the patient was maintained within one degree (1° C.) of the temperature of the blood withdrawn from the patient. The patient was given 2000 units of sodium heparin before each treatment and 20 mg protamine sulfate after each treatment to reverse the effects of the sodium heparin. Additionally, 1000 units of sodium heparin were pumped into the ultrafiltration system during each treatment to prevent clotting within the system. A volume of ultrafiltrate removed from the patient was replaced by ultrafiltrate taken from the blood of healthy males prior to the treatment. The amount replaced was at least equivalent to the volume of ultrafiltrate removed from the patient. Additionally, the ultrafiltration system was flushed with saline solution after the treatment to return blood remaining in the system to the patient. The catheters remained in place during the several treatments. The treatment data is set forth in the table below.

| Treatment No. | Day | Blood Flow Rate. cc/min | Total Permeate cc | Treatment Period Min. | Press. Drop Across membrane mmHg |
| --- | --- | --- | --- | --- | --- |
| 1 | 1 | 150 | 205 | 30 | 115–120 |
| 2 | 5 | 120 | 315 | 45 | 115–120 |
| 3 | 8 | 150 | 315 | 45 | 115–120 |
| 4 | 12 | 150 | 385 | 45 | 125 |
| 5 | 14 | 150 | 385 | 45 | 125 |
| 6 | 16 | 150 | 385 | 45 | 125 |

Within 24 hours of each treatment, the patient experienced pain and exhibited edema and erythemia in the left shoulder and other areas where known tumors were located. Moreover, a significant increase was noted (i.e., up to 5° C.) in the temperature of the left shoulder area over the right shoulder area although the patient was afebrile. After the first three treatments the pain, swelling and redness of the tumor areas were at the highest levels. Thereafter, the severity thereof decreased considerably. The patient's clinical response to the treatment was consistent with accute cell mediated responses to the malignant growths. Moreover, a serum electrophoresis after the third treatment showed an elevation of fibrinogen in the Alph-1 fraction which indicates acute tumor necrosis. After the fourth treatment, a chest X-ray of the patient showed an increased interstitial water density about right pulmonary nodules in a classical pattern of pulmonary infiltration. The infiltrate, however, was confined to the areas of the nodules which is an indication of an acute immune response to the tumor.

The treatment of human patients is essentially the same as those described above for animals except that the brachiocephalic or subclavian veins can be used to withdraw blood in lieu of the jugular vein as used with smaller animals, because in humans these veins are usually large enough to be used.

The advantages of the process and system for human treatment in accordance with the invention are many. There are essentially no significant, clinically observable side effects to the treatment. Except for the sodium heparin and the nutrients, salts and vitamins which are returned to the patient, no foreign chemicals are introduced into the patient's body. The risks of the treatment are essentially no greater than dialysis and other similar treatments. The equipment and procedures are very simple and thus the treatment costs are very small in comparison with conventional procedures of surgery, radiation or chemotherapy. Very importantly, the treatment can be conducted on an out patient basis, so there is little inconvenience to the patient.

The usual treatment of patients in accordance with this invention will be a continuous process wherein during the treatment period, blood is continuously removed from the patient and passed through the separation unit to remove the fraction containing the immunosuppressive components. Treated blood is returned to the patient in a continual fashion to initiate the immune response against the diseased tissue or condition. In some circumstances, however, it may be desirable to replace the blood taken from the patient with blood previously treated to remove immunosuppressive components in which case the blood withdrawn from the patient can be treated to remove blocking agents and then stored for subsequent use.

It is obvious that modifications and improvements can be made to the above described method and system without departing from the inventive concepts thereof. For example, although not as efficient as the preferred embodiment, the blood from the patient can be first treated to separate plasma therefrom by suitable means. The separated plasma can be subjected to ultrafiltration to remove the low molecular weight immunosuppressive components therefrom and then the treated plasma and blood can be returned to the patient to initiate an immune response in accordance with the invention. Other modifications can also be made.

I claim:

1. A method of extracorporeally treating a mammalian patient having a dysfunction of the immune system thereof wherein immunosuppressive components having molecular weights less than 200,000 Daltons retard or prevent immune system response, the method including a plurality of treatments with each treatment comprising:
   (a) withdrawing whole blood comprising a cellular fraction and a plasma fraction from a patient having such a dysfunction;
   (b) selectively separating from the withdrawn whole blood components of the plasma fraction with molecular weights less than 200,000 Daltons including the immunosuppressive components which retard or prevent immune system response to the immune system dysfunction; and
   (c) returning to the patient whole blood from which the components of the plasma fraction have been separated; and
   (d) continuing the treatment until the concentration of immunosuppressive components with molecular weights less than 200,000 Daltons in the extracellular fluid of the patient are reduced to a level sufficient to initiate an immune system response.

2. The method of claim 1 wherein the blood fraction is selectively separated from the blood without separating high molecular weight components including blood cells and platelets from plasma.

3. The method of claim 1 wherein the blood fraction is selectively separated from the blood by passing the withdrawn blood through an ultrafilter to remove therefrom the blood fraction as ultrafiltrate or permeate.

4. The method of claim 1 wherein components of the plasma fraction with molecular weights less than about 200,000 Daltons are selectively separated from the withdrawn whole blood by ultrafiltration with an ultrafiltration medium having an effective pore size from about 0.03 to less than about 0.10 micron.

5. The method of claim 4 wherein the blood fraction is selectively separated from the blood by ultrafiltration with an ultrafiltration medium having an effective pore size from about 0.03 to about 0.07 micron.

6. The method of claim 1 wherein liquid is returned to the patient from which the blood is withdrawn to replace the liquid lost from the withdrawn blood when the plasma components are separated therefrom.

7. The method of claim 6 wherein at least one member of the group consisting of nutrients, vitamins and salts is added to the liquid returned to the mammal from which the blood is withdrawn to replace those which are lost from the withdrawn blood when the plasma fraction is separated therefrom.

8. The method of treating a mammalian patient with cancer or other neoplastic tissue, the growth or continuation of which results from or depends upon a dysfunction of the immune system thereof wherein immunosuppressive components having molecular weights less then 200,000 Daltons retard or prevent immune system response, the method including a plurality of treatments with each treatment comprising:
  (a) withdrawing whole blood which includes a cellular fraction and a plasma fraction from a patient with cancer or other neoplastic tissue;
  (b) selectively separating from the withdrawn whole blood components of the plasma fraction having molecular weights less than 200,000 Daltons including the immunosuppressive components which retard or prevent immune system response to cancer or other neoplastic tissue;
  (c) returning to the patient whole blood from which the components of the plasma fraction have been removed; and
  (d) the treatment continuing until the concentration of immunosuppressive components with molecular weights less than 200,000 Daltons in the extracellular fluid of the patient is reduced to a level sufficient to initiate an immune system response to the cancer or neoplastic tissue.

9. The method of claim 8 wherein the treatment is repeated on a plurality of occasions until the cancer or neoplastic tissue has been essentially destroyed or until the cancer or neoplastic tissue can be surgically removed or otherwise treated.

10. The method of claim 8 wherein blood fraction is selectively separated from the withdrawn blood by ultrafiltration with an ultrafilter medium having an effective pore size from about 0.03 to less than about 0.10 micron.

11. The method of claim 8 wherein liquid is returned to the patient from which the blood is withdrawn to replace the liquid lost from the withdrawn blood when the plasma components are separated therefrom.

12. The method of claim 11 wherein at least one member of the group consisting of nutrients, vitamins and salts is added to the liquid returned to the patient from which the blood was withdrawn to replace those which are lost from the withdrawn blood when the plasma fraction is separated therefrom.

13. The method of claim 12 wherein the lost nutrients, vitamins and salts are returned in a volume of liquid essentially equivalent to the volume of blood fraction separated.

* * * * *